US00PP32353P2

(12) United States Plant Patent
Weisel

(10) Patent No.: US PP32,353 P2
(45) Date of Patent: Oct. 20, 2020

(54) ***LANTANA* PLANT NAMED 'TSF002'**

(50) Latin Name: *Lantana montevidensis*
Varietal Denomination: TSF002

(71) Applicant: Lawrence Harold Weisel, Escondido, CA (US)

(72) Inventor: Lawrence Harold Weisel, Escondido, CA (US)

(73) Assignee: Treesap Farms, LLC, Houston, TX (US)

( * ) Notice: Subject to any disclaimer, the term of this patent is extended or adjusted under 35 U.S.C. 154(b) by 0 days.

(21) Appl. No.: 16/602,183

(22) Filed: Aug. 23, 2019

(51) Int. Cl.
*A01H 5/02* (2018.01)
*A01H 6/86* (2018.01)

(52) U.S. Cl.
USPC ..... Plt./227

(58) Field of Classification Search
USPC ..... Plt./226, 227
See application file for complete search history.

*Primary Examiner* — Susan McCormick Ewoldt
*Assistant Examiner* — Karen M Redden
(74) *Attorney, Agent, or Firm* — C. A. Whealy

(57) ABSTRACT

A new and distinct cultivar of *Lantana* plant named 'TSF002', characterized by its compact, outwardly spreading to trailing plant habit; moderately vigorous growth habit; freely branching growth habit; medium green-colored leaves; relatively large inflorescences with flowers that are strong reddish purple in color; and good garden performance.

2 Drawing Sheets

Botanical designation: *Lantana montevidensis*.
Cultivar denomination: 'TSF002'.

BACKGROUND OF THE INVENTION

The present invention relates to a new and distinct cultivar of *Lantana* plant, botanically known as *Lantana montevidensis* and hereinafter referred to by the name 'TSF002'.

The new *Lantana* plant is a naturally-occurring whole plant mutation of an unnamed selection of *Lantana montevidensis*, not patented. The new *Lantana* plant was discovered and selected by the Inventor as a single flowering plant from within a population of plants of the parent selection in a controlled greenhouse environment in Orange, Calif. in March, 2017.

Asexual reproduction of the new *Lantana* plant by vegetative terminal cuttings in a controlled greenhouse environment in Escondido, Calif. since April, 2017 has shown that the unique features of this new *Lantana* plant are stable and reproduced true to type in successive generations.

SUMMARY OF THE INVENTION

Plants of the new *Lantana* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'TSF002'. These characteristics in combination distinguish 'TSF002' as a new and distinct *Lantana* plant:

1. Compact, outwardly spreading to trailing plant habit.
2. Moderately vigorous growth habit.
3. Freely branching growth habit.
4. Medium green-colored leaves.

5. Relatively large inflorescences with flowers that are strong reddish purple in color.
6. Good garden performance.

Plants of the new *Lantana* can be compared to plants of the parent selection. Plants of the new *Lantana* differ primarily from plants of the parent selection in the following characteristics:

1. Plants of the new *Lantana* have larger inflorescences than plants of the parent selection.
2. Plants of the new *Lantana* have darker green-colored peduncles than plants of the parent selection.

Plants of the new *Lantana* can be compared to plants of the *Lantana montevidensis* 'Spreading White', not patented. In side-by-side comparisons, plants of the new *Lantana* differ from plants of 'Spreading White' in the following characteristics:

1. Plants of the new *Lantana* have larger inflorescences than plants of 'Spreading White'.
2. Plants of the new *Lantana* have strong reddish purple-colored flowers whereas plants of 'Spreading White' have white-colored flowers.

Plants of the new *Lantana* can also be compared to plants of the *Lantana camara* 'Radiation', not patented. In side-by-side comparisons, plants of the new *Lantana* differ from plants of 'Radiation' in the following characteristics:

1. Plants of the new *Lantana* have larger inflorescences than plants of 'Radiation'.
2. Plants of the new *Lantana* have strong reddish purple-colored flowers whereas plants of 'Radiation' have orange red and yellow-colored flowers.

BRIEF DESCRIPTION OF THE PHOTOGRAPHS

The accompanying colored photographs illustrate the overall appearance of the new *Lantana* plant showing the colors as true as it is reasonably possible to obtain in colored reproductions of this type. Colors in the photographs may differ slightly from the color values cited in the detailed botanical description which accurately describe the colors of the new *Lantana* plant.

The photograph on the first sheet is a side perspective view of a typical flowering plant of 'TSF002' grown in a container.

The photograph on the second sheet is a close-up view of a typical flowering plant of 'TSF002'.

DETAILED BOTANICAL DESCRIPTION

The aforementioned photographs and following observations and measurements describe plants grown during the summer in one-gallon in a polyethylene-covered greenhouse in Escondido, Calif. and under commercial practices typical of commercial *Lantana* production. During the production of the plants, day temperatures averaged 30° C. and night temperatures averaged 16° C. Plants were pinched and were six months old when the photographs and the description were taken. In the following description, color references are made to The Royal Horticultural Society Colour Chart, Fifth Edition 2015, except where general terms of ordinary dictionary significance are used.

Botanical classification: *Lantana montevidensis* 'TSF002'.

Parentage: Naturally-occurring whole plant mutation of an unnamed selection of *Lantana montevidensis*, not patented.

Propagation:

- *Type*.—By vegetative terminal cuttings.
- *Time to initiate roots, summer and winter*.—About seven to ten days at soil temperatures about 27° C.
- *Time to produce a rooted young plant, summer*.—About three weeks at soil temperatures about 27° C.
- *Time to produce a rooted young plant, winter*.—About one month at soil temperatures about 18° C.
- *Root description*.—Fibrous; medium in thickness; typically light brown to white in color, actual color of the roots is dependent on substrate composition, water quality, fertilizer type and formulation, substrate temperature and physiological age of roots.
- *Rooting habit*.—Freely branching; dense.

Plant description:

- *Plant and growth habit*.—Compact, outwardly spreading to trailing plant habit; moderately vigorous growth habit; freely branching growth habit.
- *Plant height*.—About 12 cm.
- *Plant diameter*.—About 60 cm to 70 cm.

Lateral branch description:

- *Branching habit*.—Freely branching habit with potentially two lateral branches developing at every node; pinching enhances lateral branch development.
- *Length*.—About 40 cm to 50 cm.
- *Diameter*.—About 4 mm to 6 mm.
- *Internode length*.—About 3 cm.
- *Strength*.—Strong, flexible.
- *Texture and luster, when developing*.—Fine pubescence; matte.
- *Texture and luster, fully developed*.—Woody, smooth; matte.
- *Color, when developing*.—Close to 144A and 144B then becoming closer to 164A.
- *Color, fully developed*.—Close to 199B to 199C.

Leaf description:

- *Arrangement*.—Opposite, simple.
- *Length*.—About 3.75 cm.
- *Width*.—About 2.7 cm.
- *Shape*.—Broadly ovate.
- *Apex*.—Acute.
- *Base*.—Obtuse.
- *Margin*.—Crenate to dentate.
- *Texture and luster, upper and lower surfaces*.—Smooth, glabrous; matte.
- *Venation pattern*.—Pinnate, reticulate.
- *Color*.—Developing leaves, upper surface: More green than 146A. Developing leaves, lower surface: Close to 144A. Fully expanded leaves, upper surface: Darker green than 146A; venation, darker green than 146A. Fully expanded leaves, lower surface: Close to 146B; venation, close to 146C.
- *Petioles*.—Length: About 5 mm to 6 mm. Diameter: About 1 mm. Strength: Strong, flexible. Texture and luster, upper and lower surfaces: Smooth, glabrous; matte. Color, upper surface: Close to 146B to 146C. Color, lower surface: Close to 146C to 146D.

Flower description:

- *Flower arrangement and flowering habit*.—Solitary salverform flowers arranged in terminal and axillary hemispherical umbels; flowers face mostly upward or outward; freely flowering habit with about 20 flowers developing per inflorescence and numerous inflorescences developing per plant during the flowering season.
- *Natural flowering season*.—Early flowering habit, plants begin flowering about three weeks from planting rooted cuttings; long flowering period, plants of the new *Lantana* flower year round in Southern California.
- *Flower longevity on the plant*.—About one week; flowers not persistent; inflorescences last about two weeks.
- *Fragrance*.—Mildly fragrant; pleasant.
- *Flowers*.—Appearance: Flared trumpet, corolla fused, four-parted; flowers are sessile. Diameter: About 1 cm. Depth (height): About 1.4 cm.
- *Flower buds*.—Length: About 4 mm. Diameter: About 3 mm. Shape: Ovoid Color: Close to 143A.
- *Corolla*.—Arrangement: Single whorl of four fused petals. Petal lobe length: About 4 mm to 5 mm. Petal lobe width: About 4 mm to 5 mm. Petal lobe shape: Roughly spatulate. Petal lobe apex: Rounded. Petal margin: Entire. Petal texture and luster, upper and lower surfaces: Smooth, glabrous; matte. Throat texture and luster: Smooth, glabrous; matte. Tube texture and luster: Fine pubescence; matte. Color: When opening, upper and lower surfaces: Close to NN74A. Fully opened, upper surface: Close to NN74A; color does not change with development. Fully opened, lower surface: Close to NN74A to NN74B; color does not change with development. Throat: Initially, close to NN74A; color becoming closer to NN155D (distally) and 9A (proximally) with development. Tube: Distally, close to NN74A to NN74B; proximally, close to NN155D; color does not change with development.
- *Calyx*.—Appearance: Tubular calyx with about 20 fused sepals; one subtending each individual flower. Length: About 1 cm. Diameter: About 1.2 mm. Sepal shape: Ovate. Sepal apex: Acute. Sepal margin: Entire. Sepal texture and luster, upper and lower surfaces: Smooth, glabrous; slightly glossy. Sepal color, upper and lower surfaces: Close to 144A.

*Peduncles*.—Length: About 3 cm. Diameter: About 1 mm. Strength: Strong, flexible. Aspect: About 45° from stem axis. Texture and luster: Smooth, glabrous; matte. Color: Close to 144A.

*Reproductive organs*.—Stamens: To date, stamen development has not been observed on plants of the new *Lantana*. Pistils: To date, pistil development has not been observed on plants of the new *Lantana*. Fruits and seeds: To date, fruit and seed development have not been observed on plants of the new *Lantana*.

Garden performance: Plants of the new *Lantana* have been observed to have good garden performance and to tolerate wind and rain and temperatures from 0° C. to 40° C.

Pathogen & pest tolerance: To date, plants of the new *Lantana* have not been observed to be tolerant to pathogens and pests common to *Lantana* plants.

It is claimed:

1. A new and distinct *Lantana* plant named 'TSF002' as illustrated and described.

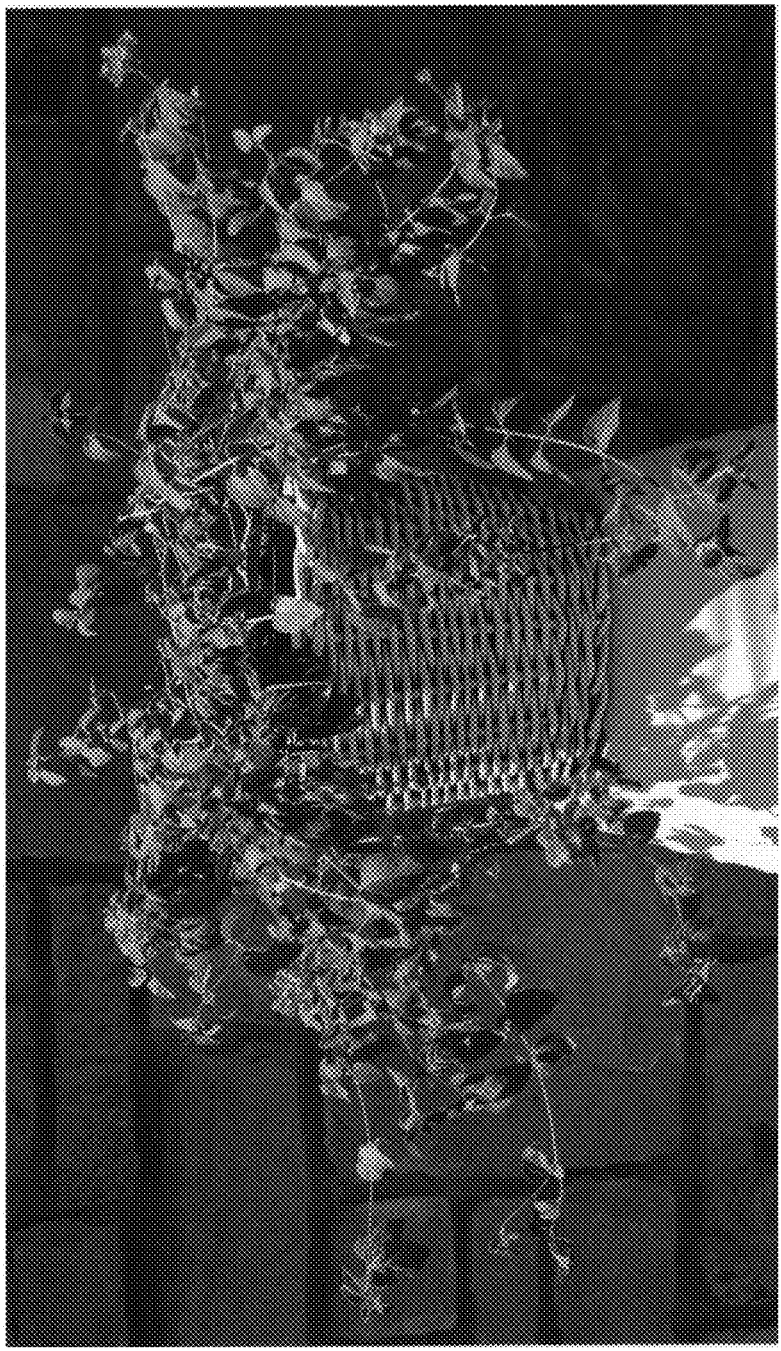

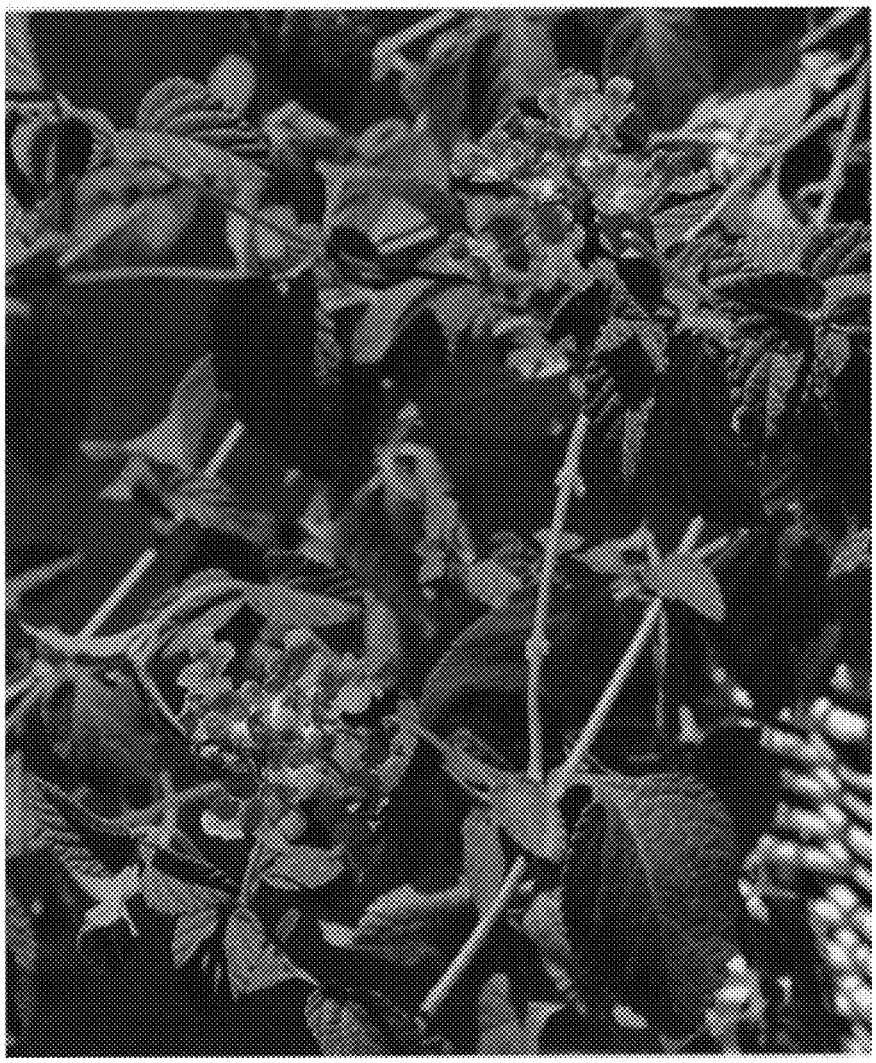

* * * * *